(12) United States Patent
Andree et al.

(10) Patent No.: US 6,448,203 B1
(45) Date of Patent: Sep. 10, 2002

(54) SUBSTITUTED ARYLURACILS

(75) Inventors: Roland Andree, Langenfeld (DE); Markus Dollinger, Overland Park, KS (US); Christoph Erdelen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,438

(22) PCT Filed: Mar. 30, 1998

(86) PCT No.: PCT/EP98/01847
§ 371 (c)(1),
(2), (4) Date: Oct. 7, 1999

(87) PCT Pub. No.: WO98/46592
PCT Pub. Date: Oct. 22, 1998

(30) Foreign Application Priority Data

Apr. 11, 1997 (DE) .......................... 197 15 017

(51) Int. Cl.⁷ .................. C07D 401/12; C07D 403/12; C07D 405/12; A01N 43/54
(52) U.S. Cl. ................. 504/243; 544/311; 544/312; 544/313; 544/314; 544/310; 544/284; 544/295; 544/296; 504/240; 504/235; 504/236; 504/237; 504/238
(58) Field of Search .................. 504/243, 240, 504/237; 544/311, 312, 313, 314, 295, 296, 310, 284

(56) References Cited

U.S. PATENT DOCUMENTS 4,423,237 A 12/1983 Baker .................. 549/362
5,344,812 A 9/1994 Theodoridis ............. 504/243
5,399,543 A 3/1995 Theodoridis ............. 504/243

FOREIGN PATENT DOCUMENTS

| CA | 2083071 | 6/1993 |
|---|---|---|
| JP | 4-178373 | 6/1992 |
| JP | 5-39272 | 2/1993 |
| JP | 5-202031 | 8/1993 |
| WO | 95/17096 | 6/1995 |

OTHER PUBLICATIONS

J. Heterocycl. Chem. 9, Jun. 1972, pp. 513–522, Novel 6–(Trifluoromethyl)cytosines and 6–(Trifluoromethyl)uracils, Albert W. Lutz and Susan H. Trotto.

*Primary Examiner*—John M. Ford
(74) *Attorney, Agent, or Firm*—Joseph C. Gil; Raymond J. Harmuth; James R. Franks

(57) ABSTRACT

The invention relates to novel substituted aryluracils of the formula (I):

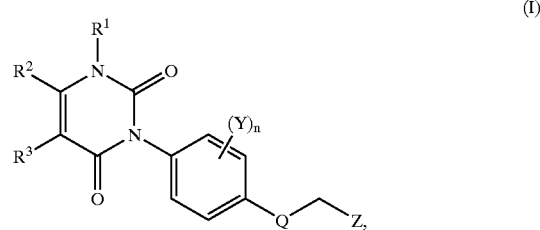

to processes for their preparation and to their use as crop protection agents.

5 Claims, No Drawings

SUBSTITUTED ARYLURACILS

This is a 371 of PCT EP 98/01847 filed Mar. 30, 1998.

TECHNICAL FIELD OF THE INVENTION

The invention relates to novel substituted aryluracils, to processes for their preparation and to their use as crop protection agents, in particular as herbicides and insecticides.

BACKGROUND OF THE INVENTION

A large number of substituted aryluracils are already known from the (patent) literature (cf. JP 05202031, JP 05039272, U.S. Pat. No. 5344812, U.S. Pat. No. 5399543, WO 9511096). However, these compounds have hitherto not attained any particular importance.

DETAILED DESCRIPTION OF THE INVENTION

This invention, accordingly, provides novel substituted aryluracils of the general formula (I)

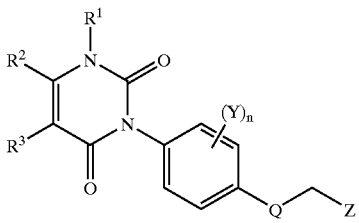

in which
n represents the numbers 0, 1, 2 or 3,
Q represents O, S, SO or $SO_2$,
$R_1$ represents hydrogen, amino or optionally substituted alkyl,
$R^2$ represents carboxyl, cyano, carbamoyl, thiocarbamoyl or in each case optionally substituted alkyl or alkoxycarbonyl,
$R^3$ represents hydrogen, halogen or optionally substituted alkyl.
Y represents nitro, amino, hydroxyl, carboxyl, cyano, carbamoyl, thiocarbamoyl, sulpho, chlorosulphonyl, aminosulphonyl, halogen, or represents in each case optionally substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino or alkylsulphonylamino, and
z represents optionally substituted heterocyclyl from the series furyl, tetrahydrofuryl, benzofuryl, dihydrobenzofuryl, dioxolanyl, dioxanyl, benzodioxanyl, pyrrolyl, pyrazolyl, irnidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, or represents in each case substituted thiazolyl, isothiazolyl, benzothiazolyl or benzimidazolyl.

The novel substituted aryluracils of the general formula (I) are obtained when
(a) aminoalkenoic esters of the general formula (II)

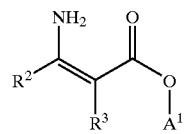

in which
$R^2$ and $R^3$ are each as defined above and
$A^1$ represents alkyl, aryl or arylalkyl
are reacted with arylurethanes (arylcarbamates) of the general formula (III)

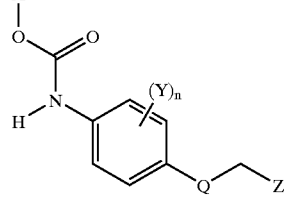

in which
n, Q, Y and Z are each as defined above and
$A^2$ represents alkyl, aryl or arylalkyl,
if appropriate in the presence of a reaction auxiliary and if appropriate in the presence of a diluent,
or when
(b) substituted aryluracils of the general formula (IV)

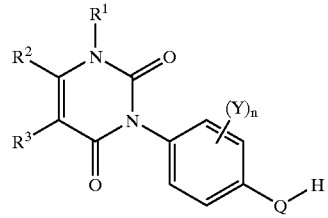

in which
n, Q, $R^1$, $R^2$, $R^3$ and Y are each as defined above
are reacted with halogenomethylheterocycles of the general formula (V)

in which
Z is as defined above and
X represents halogen,
if appropriate in the presence of a reaction auxiliary and if appropriate in the presence of a diluent, or when
(c) substituted aryluracils of the general formula (Ia)

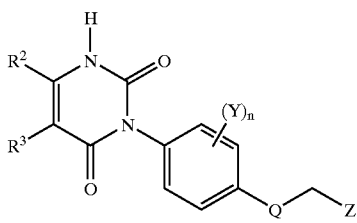

in which
n, Q, $R^2$, $R^3$, Y and Z are each as defined above
are reacted with 1-arninooxy-2,4-dinitro-benzene or with alkylating agents of the general formula (VI)

 (VI)

in which
$A^3$ represents optionally substituted alkyl and
$X^1$ represents halogen or the grouping —O—$SO_2$—O—$A^3$.
if appropriate in the presence of a reaction auxiliary and if appropriate in the presence of a diluent, The novel substituted aryluracils of the general formula (I) have strong herbicidal and insecticidal activity.

The invention preferably provices compounds of the formula (I) in which n represents the numbers 0, 1, 2 or 3, Q represents O, S, SO or $SO_2$, $R_1$ represents hydrogen, amino or optionally cyano-, halogen-, or $C_1$–$C_4$-alkoxy-substituted alkyl having 1 to 4 carbon atoms, $R^2$ represents carboxyl, cyano, carbamoyl, thiocarbamoyl or represents in each case optionally cyano-, halogen- or $C_1$–$C_4$-alkoxy-substituted alkyl or alkoxycarbonyl having in each case 1 to 4 carbon atoms, $R^3$ represents hydrogen, halogen or optionally halogen-substituted alkyl having 1 to 4 carbon atoms, Y represents nitro, amino, hydroxyl, carboxyl, cyano, carbamoyl, thiocarbamoyl, sulpho, chlorosulphonyl, aminosulphonyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino or alkylsulphonylamino having in each case 1 to 4 carbon atoms in the alkyl groups, and Z represents optionally substituted heterocyclyl from the group consisting of furyl, tetrahydrofuryl, benzofuryl, dihydrobenzofuryl, dioxolanyl, dioxanyl, benzodioxanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, or represents in each case substituted thiazolyl, isothiazolyl, benzothiazolyl or benzimidazolyl, where the possible substituents are preferably selected from the list below:
nitro, amino, hydroxyl, carboxyl, cyano, carbamoyl, thiocarbamoyl, sulpho, chlorosulphonyl, aminosulphonyl, halogen, in each case optionally cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino or alkylsulphonylamino having in each case 1 to 4 carbon atoms in the alkyl groups or phenyl.

The invention relates in particular to compounds of the formula (I) in which n represents the numbers 0, 1 or 2, Q represents O, S, SO or $SO_2$, $R^1$ represents hydrogen, amino or in each case optionally cyano-, fluorine-, chlorine-, methoxy- or ethoxy-substituted methyl or ethyl, $R^2$ represents in each case optionally fluorine- and/or chlorine-substituted methyl or ethyl, $R^3$ represents hydrogen, fluorine, chlorine, bromine or methyl, Y represents nitro, amino, hydroxyl, carboxyl, cyano, carbamoyl, thiocarbamoyl, sulpho, chlorosulphonyl, aminosulphonyl, fluorine, chlorine, bromine or represents in each case optionally cyano-, fluorine-, chlorine-, bromine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylarnino, n- or i-butyroylamino, methoxycarbonylamino, ethoxycarbonylamino, methylsulphonylamino, ethylsulphonylamino, n- or i-propylsulphonylamino, n-, i-, s- or t-butylsulphonylamino, and Z represents optionally substituted heterocyclyl from the group consisting of furyl, tetrahydrofuryl, benzofuryl, dihydrobenzofuryl, dioxolanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, or represents in each case substituted thiazolyl, benzothiazolyl or benzimidazolyl, where the possible substituents are preferably selected from the list below:
nitro, amino, hydroxyl, carboxyl, cyano, carbamoyl, thiocarbamoyl, sulpho, chlorosulphonyl, aminosulphonyl, fluorine, chlorine, bromine, in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulphonylamino, ethylsulphonylamino, n- or i-propylsulphonylamino, n-, i-, s- or t-butylsulphonylamino, phenyl.

Very particular preference is given to substituted aryluracils of the formula (Ib)

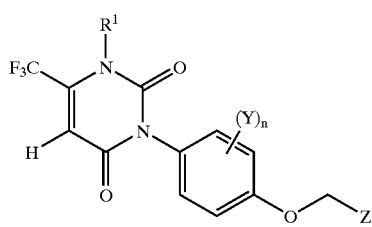

in which
- $R^1$ represents hydrogen, amino or methyl,
- Y represents hydrogen, ortho-fluorine, meta-$COOC_2H_5$ or meta-$NHSO_2C_2H_5$ and
- Z represents a heterocycle from the group

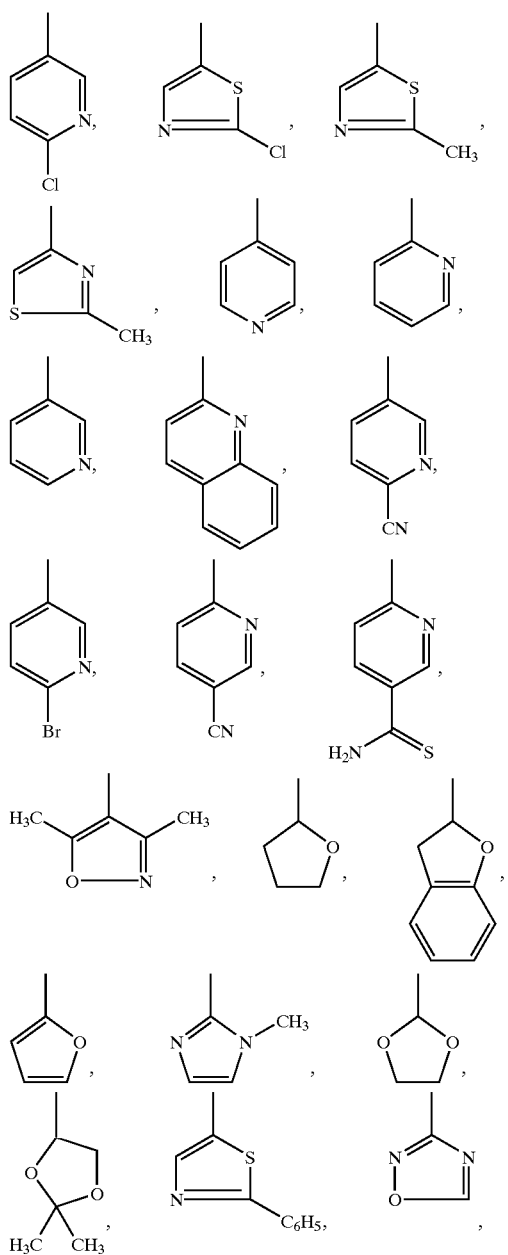

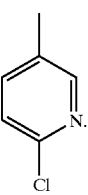

The abovementioned general or preferred radical definitions apply both to the end products of the formula (I) and, correspondingly, to the starting materials or intermediates required for the preparation. These radical definitions can be combined with each other at will, i.e. including combinations between the given preferred ranges.

Using, for example, methyl 3-amino-2,4,4,4-tetrafluoro-crotonate and -methyl N-[2-fluoro-4-(2,4-dichloro-thiazol-5-yl-methylthio)-phenyl]-carbamate as starting materials, the course of the reaction in the process (a) according to the invention can be illustrated by the following equation:

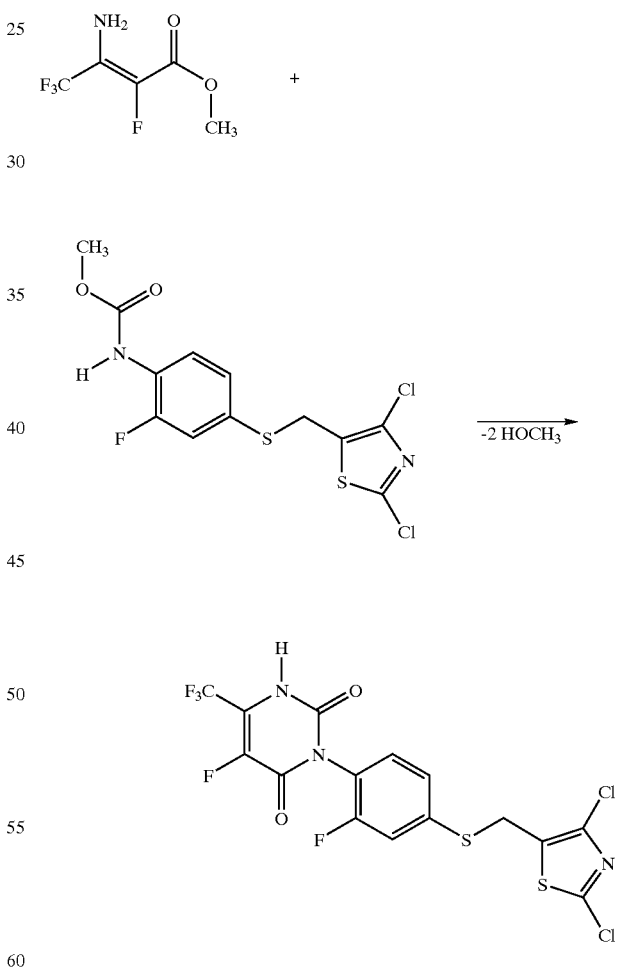

Using, for example, 1-(4-hydroxy-3-nitro-phenyl)-4-trifluoromethyl-3,6-dihydro-2,6-dioxo-1(2H)-pyrimidine and 2-chloromethyl-furan as starting materials, the course of the reaction in the process (b) according to the invention can be illustrated by the following equation:

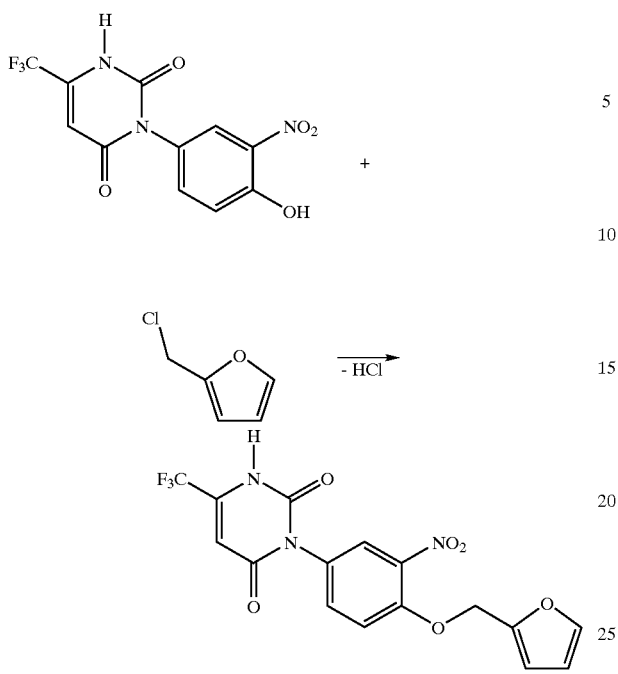

Using, for example, 1-[3-chloro-4-(3,5-dimethyl-isoxazol4-yl-methoxy)-phenyl]-5-chloro4-chlorodifluoromethyl-3,6-dihydro-2,6-dioxo- 1(2H)-pyrimidine and ethyl bromide as starting materials, the course of the reaction in the process (c) according to the invention can be illustrated by the following equation:

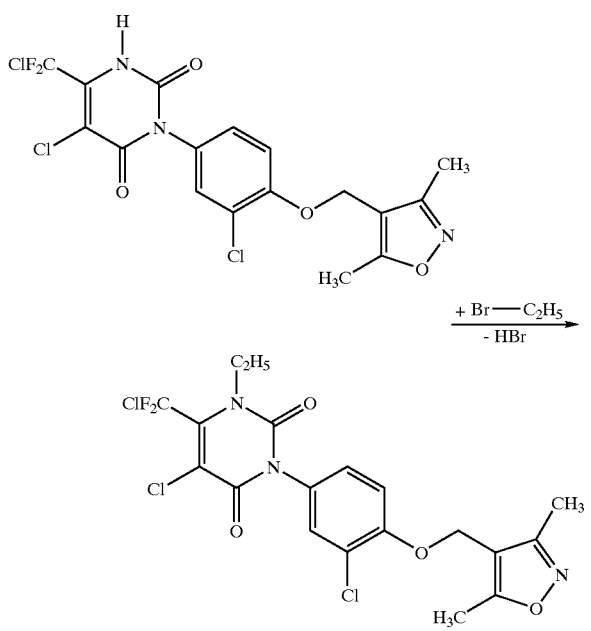

The formula (II) provides a general definition of the aminoalkenoic esters to be used as starting materials in the process (a) according to the invention for preparing compounds of the formula (I). In the formula (II), $R^2$ and $R^3$ each preferably or in particular have those meanings which have already been mentioned above, in connection with the description of the compounds of the formula (I) according to the invention, as being preferred or as being particularly preferred for $R^2$ and $R^3$; $A^1$ preferably represents $C_1$–$C_4$-alkyl, phenyl or benzyl, in particular methyl or ethyl.

The starting materials of the general formula (II) are known and/or can be prepared by known processes (cf. J. Heterocycl. Chem. 9 (1972), 513–522).

The formula (III) provides a general definition of the arylurethanes (arylcarbamates) further to be used as starting materials in the process (a) according to the invention. In the formula (III), n, Q, Y and Z each preferably or in particular have those meanings which have already been mentioned above, in connection with the description of the compounds of the formula (I) according to the invention, as being preferred or as being particularly preferred for n, Q, Y and Z; $A^2$ preferably represents $C_1$–$C_4$-alkyl, phenyl or benzyl, in particular methyl or ethyl.

The starting materials of the general formula (III) are known and/or can be prepared by known processes (cf. U.S. Pat. No. 4193787, U.S. Pat. No. 4423237).

The arylurethanes (arylcarbamates) of the general formula (III) are obtained, for example, when arylamines of the general formula (VII)

in which
n, Q, Y and Z are each as defined above
are reacted with chloroformic esters of the general formula (VIII)

$$A^2\text{—}O\text{—}CO\text{—}Cl \qquad (VIII)$$

in which
$A^2$ is as defined above,
if appropriate in the presence of an acid acceptor, such as, for example, pyridine, and if appropriate in the presence of a diluent, such as, for example, methylene chloride, at temperatures between 0° C. and 100° C. (cf. the Preparation Examples).

The formula (IV) provides a general definition of the substituted aryluracils to be used as starting materials in the process (b) according to the invention for preparing compounds of the formula (I). In the formula (IV), n, Q, $R^2$, $R^3$ and Y each preferably or in particular have those meanings which have already been mentioned above, in connection with the description of the compounds of the formula (I) according to the invention, as being preferred or as being particularly preferred for n, Q, $R^2$, $R^3$ and Y.

The starting materials of the general formula (IV) are known and/or can be prepared by known processes (cf. EP 545206, JP 04178373, U.S. Pat. No. 5344812, U.S. Pat. No. 5399543, WO 9517096).

The formula (V) provides a general definition of the halogenomethylheterocycles further to be used as starting materials in the process (b) according to the invention. In the formula (V), Z preferably or in particular has those meanings which have already been mentioned above, in connection with the description of the compounds of the formula (I) according to the invention, as being preferred or as being particularly preferred for Z; X preferably represents fluorine, chlorine, bromine or iodine, in particular chlorine or bromine.

The starting materials of the general formula (V) are known organic chemicals for synthesis.

The formula (Ia) provides a general definition of the substituted aryluracils to be used as starting materials in the process (c) according to the invention for preparing compounds of the formula I. In the formula (Ia), n, Q, $R^2$, $R^3$, Y and Z each preferably or in particular have those meanings which have already been mentioned above, in connection with the description of the compounds of the formula (I) according to the invention, as being preferred or as being particularly preferred for n, Q, $R^2$, $R^3$, Y and Z.

As novel compounds, the starting materials of the general formula (Ia) for the process (c) also form part of the subject-matter of the present application; they can be prepared according to the processes (a) or (b) according to the invention.

The formula (IV) provides a general definition of the alkylating agents further to be used as starting materials in the process (c) according to the invention. In the formula (IV), $R^1$ and $R^2$ each preferably or in particular have those meanings which have already been mentioned above, in connection with the description of the compounds of the formula (I) according to the invention, as being preferred or as being particularly preferred for $R^1$ and $R^2$.

In the formula (IV),
$A^3$ preferably represents optionally cyano-, fluorine- or chlorine-substituted alkyl having 1 to 4 carbon atoms, in particular methyl or ethyl, and X preferably represents fluorine, chlorine, bromine or iodine, or represents the grouping —O—$SO_2$—O—$A^3$, in particular chlorine or bromine.

The starting materials of the formula (IV) are known organic chemicals for synthesis.

Suitable reaction auxiliaries for the processes (a), (b) and (c) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methylpyridine, 4-dimethylamino-pyridine, N-methyl-piperidine, 1,4-diazabicyclo[2,2,2]-octane (DABCO), 1,5-diazabicyclo[4,3,0]-non-5-ene (DBN) or 1,8-diazabicyclo[5,4,0]-undec-7-ene (DBU).

Suitable diluents for carrying out the processes (a), (b) and (c) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitrites, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, and also sulphoxides or sulphones, such as dimethyl sulphoxide or tetramethylene sulphone ("sulpholane").

When carrying out the processes (a), (b) and (c) according to the invention, the reaction temperatures can be varied within a relatively wide range. In general, the reaction is carried out at temperatures between 0° C. and 200° C., preferably between 10° C. and 150° C.

In general, the processes (a), (b) and (c) according to the invention are carried out under atmospheric pressure. However, it is also possible to carry out the processes according to the invention under elevated or reduced pressure—in general between 0.1 bar and 10 bar.

For carrying out the processes (a), (b) and (c) according to the invention, the starting materials are generally employed in approximately equimolar amounts. However, it is also possible in each case to employ a relatively large excess of one of the components. The reaction is generally in each case carried out in a suitable diluent in the presence of a reaction auxiliary and the reaction mixture is generally stirred for several hours at the temperature required. Work-up is in each case carried out by customary methods (cf. the Preparation Examples).

The active compounds according to the invention can be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are suitable for the control of monocotyledonous and dicotyledonous weeds by both the pre- and the post-emergence method.

The active compounds are suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include:

From the order of Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blatella germanica, Acheta domesticus*, Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bernisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, Oscinella frit, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Omithodoros spp., *Dermanyssus gallinae, Eriophyes ribis, Phyllocoptruta oleivora*, Boophilus spp., Rhipicephalus spp., Amblyommna spp., Hyalomma spp., Ixodes spp., Psoroptes spp., Chorioptes spp., Sarcoptes spp., Tarsonemus spp., Bryobia praetiosa, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp., Tylenchus spp., Helicotylenchus spp., Rotylenchus spp. and Tylenchulus spp.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and also very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol, polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are the following herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethanetsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-amrnonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfiron (ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

EXAMPLE 1

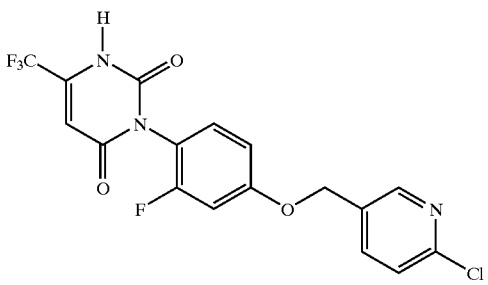

(Process (a))

A mixture of 5.5 g (25.8 mmol) of ethyl 3-amino-4,4,4-trifluoro-crotonate, 0.80 g of sodium hydride (80% pure, 28 mmol) and 40 ml of N-methyl-pyrrolidone is stirred at 40° C. for approximately 30 minutes. 8.0 g (25.8 mmol) of O-ethyl N-[2-fluoro4-(2-chloro-pyridin-5-yl-methoxy)-phenyl]-carbamate are subsequently added, and the reaction mixture is stirred at from 135° C. to 140° C. for 45 minutes. After cooling, the mixture is poured onto about twice the volume of water, shaken with diethyl ether/ethyl acetate (vol. 1/1), and the aqueous phase is acidified with 2N hydrochloric acid and shaken with ethyl acetate. The organic phase which is obtained last is washed with water, dried with sodium sulphate and filtered. The filtrate is concentrated under water pump vacuum, the residue is digested with a mixture of 2 ml of ethyl acetate, 20 ml of petroleum ether and 20 ml of diethyl ether and the resulting crystalline product is isolated by filtration with suction.

This gives 8.5 g (80% of theory) of 1-[2-fluoro-4-(2-chloro-pyridin-5-y1-methoxy)-phenyl]-4-trifluoromethyl-3,6-dihydro-2,6-dioxo-1(2H)-pyrimidine of melting point 212° C.

EXAMPLE 2

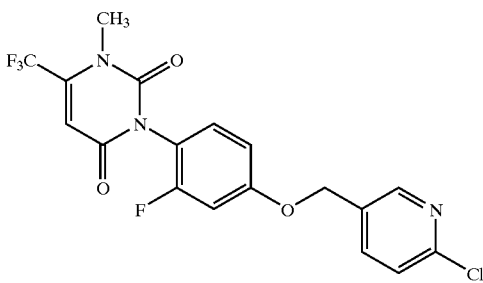

(Process (b))

A mixture of 1.5 g (3.6 mmol) of 1-[2-fluoro-4-(2-chloro-pyridin-5-yl-methoxy)-phenyl]4-trifluoromethyl-3,6-dihydro-2,6-dioxo- 1 (2H)-pyrimidine, 0.50 g (3.6 mmol) of dimethyl sulphate, 0.55 g of potassium carbonate and 20 rnl of acetone is heated under reflux for 30 minutes and then concentrated under water pump vacuum. The residue is stirred with a multi-phase system comprising aqueous 2N hydrochloric acid/ethyl acetate/petroleum ether/diethyl ether and the resulting crystalline product is isolated by filtration with suction.

This gives 1.0 g (65% of theory) of 1-[2-fluoro4-(2-chloro-pyridin-5-yl-methoxy)-phenyl]-3-methyl4-trifluoromethyl-3,6-dihydro-2,6-dioxo- 1 (2H)-pyrimidine of melting point 164° C.

EXAMPLE 3

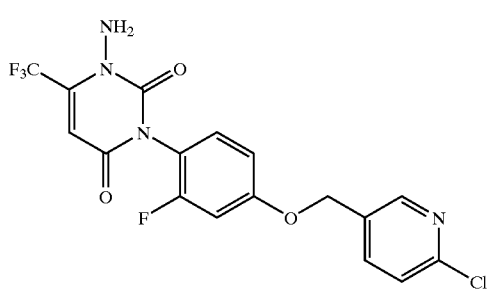

(Process (c))

A mixture of 2.0 g (4.81 mmol) of 1-[2-fluoro-4-(2-chloro-pyridin-5-yl-methoxy)-phenyl]-4-trifluoromethyl-3,6-dihydro-2,6-dioxo-1(2H)-pyrimidine, 0.42 g of sodium bicarbonate and 10 ml of N,N-dimethyl-formamide is stirred at room temperature for 30 minutes. 1.0 g (7.7 mmol) of 1-aminooxy-2,4-dinitrobenzene is added, and the reaction mixture is then stirred for two days, after addition of a further 0.4 g of 1-aminooxy-2,4-dinitro-benzene for a further two days and after addition of a further 0.4 g of 1-aminooxy-2,4-dinitro-benzene again for two days at room temperature. The mixture is shaken with water/diethyl ether and the organic phase is washed with 2N aqeuous sodium hydroxide solution, dried with sodium sulphate and filtered. The filtrate is concentrated under water pump vacuum, the residue is digested with diethyl ether and the resulting crystalline product is isolated by filtration with suction.

This gives 1.0g (50% of theory) of 3-amino-1-[2-fluoro4-(2-chloro-pyridin-5-yl-methoxy)-phenyl]4-trifluoromethyl-3,6-dihydro-2,6-dioxo- 1 (2H)-pyrimidine of melting point 171° C.

Similarly to Preparation Examples 1 to 3, and in accordance with the general description of the preparation processes according to the invention, it is also possible to prepare, for example, the compounds of the formula (I) listed in Table 1 below.

TABLE 1
Examples of compounds of the formula (I)
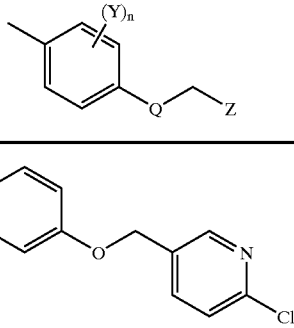
| Ex. No. | R¹ | R² | R³ | (Y)ₙ / Q / Z group | Physical data |
|---|---|---|---|---|---|
| 3 | H | CF$_3$ | H | 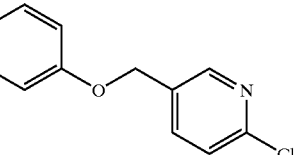 | m.p.: 243° C. |
| 4 | CH$_3$ | CF$_3$ | H | | m.p.: 184° C. |
| 5 | NH$_2$ | CF$_3$ | H | 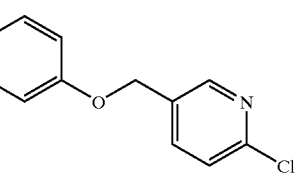 | m.p.: 181° C. |
| 6 | H | CF$_3$ | H | 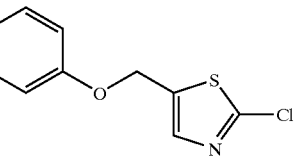 | |
| 7 | CH$_3$ | CF$_3$ | H | 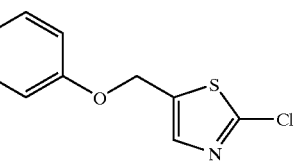 | |
| 8 | NH$_2$ | CF$_3$ | H | 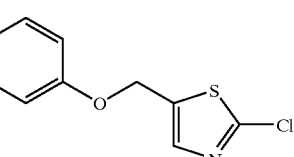 | |

TABLE 1-continued
Examples of compounds of the formula (I)
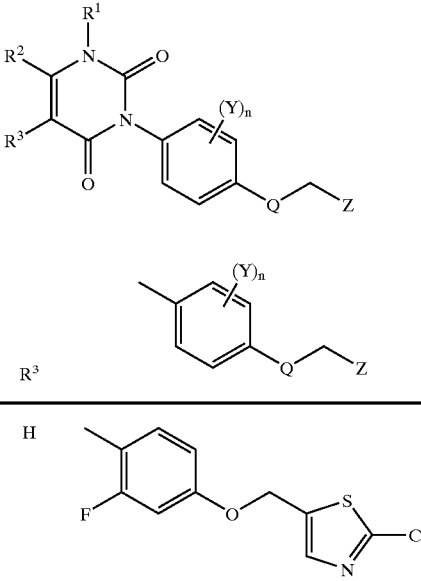
| Ex. No. | R¹ | R² | R³ | (structure) | Physical data |
|---|---|---|---|---|---|
| 9 | H | CF₃ | H | 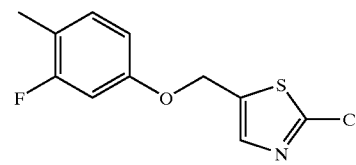 | m.p.: 145° C. |
| 10 | CH₃ | CF₃ | H | 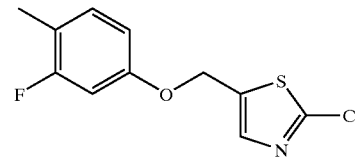 | m.p.: 120° C. |
| 11 | NH₂ | CF₃ | H | 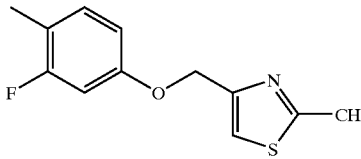 | m.p.: 192° C. |
| 12 | H | CF₃ | H | 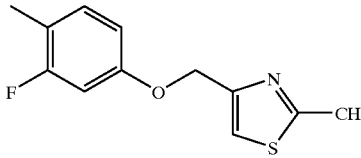 | m.p.: 200° C. |
| 13 | CH₃ | CF₃ | H | | m.p.: 136° C. |
| 14 | NH₂ | CF₃ | H | 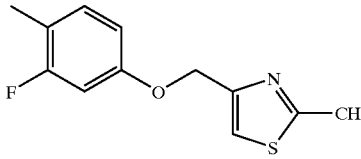 | |

TABLE 1-continued

Examples of compounds of the formula (I)

| Ex. No. | R¹ | R² | R³ | [substituted phenyl-O-CH₂-Z group] | Physical data |
|---|---|---|---|---|---|
| 15 | H | CF₃ | H | 2-(NHSO₂CH₃)-4-methylphenyl-O-CH₂-(6-chloropyridin-3-yl) | |
| 16 | CH₃ | CF₃ | H | 2-(NHSO₂C₂H₅)-4-methylphenyl-O-CH₂-(6-chloropyridin-3-yl) | m.p.: 258° C. |
| 17 | NH₂ | CF₃ | H | 2-(NHSO₂CH₃)-4-methylphenyl-O-CH₂-(6-chloropyridin-3-yl) | m.p.: 253° C. |
| 18 | H | CF₃ | H | 3-fluoro-4-methylphenyl-O-CH₂-(pyridin-4-yl) | |
| 19 | CH₃ | CF₃ | H | 3-fluoro-4-methylphenyl-O-CH₂-(pyridin-4-yl) | |
| 20 | NH₂ | CF₃ | H | 3-fluoro-4-methylphenyl-O-CH₂-(pyridin-4-yl) | |

TABLE 1-continued

Examples of compounds of the formula (I)

| Ex. No. | R¹ | R² | R³ | (substituent structure) | Physical data |
|---------|-----|-----|-----|-------------------------|---------------|
| 21 | H | CF$_3$ | H | 4-(pyridin-2-ylmethoxy)phenyl | |
| 22 | CH$_3$ | CF$_3$ | H | 4-(pyridin-2-ylmethoxy)phenyl | |
| 23 | NH$_2$ | CF$_3$ | H | 4-(pyridin-2-ylmethoxy)phenyl | |
| 24 | H | CF$_3$ | H | 4-(pyridin-3-ylmethoxy)phenyl | |
| 25 | CH$_3$ | CF$_3$ | H | 4-(pyridin-3-ylmethoxy)phenyl | |
| 26 | NH$_2$ | CF$_3$ | H | 4-(pyridin-3-ylmethoxy)phenyl | |

TABLE 1-continued

Examples of compounds of the formula (I)

| Ex. No. | R¹ | R² | R³ | n-Q-Z | Physical data |
|---|---|---|---|---|---|
| 27 | H | CF$_3$ | H | 4-(quinolin-2-ylmethoxy)phenyl | |
| 28 | CH$_3$ | CF$_3$ | H | 4-(quinolin-2-ylmethoxy)phenyl | |
| 29 | NH$_2$ | CF$_3$ | H | 4-(quinolin-2-ylmethoxy)phenyl | |
| 30 | H | CF$_3$ | H | 4-[(6-cyanopyridin-3-yl)methoxy]phenyl | |
| 31 | CH$_3$ | CF$_3$ | H | 4-[(6-cyanopyridin-3-yl)methoxy]phenyl | |
| 32 | NH$_2$ | CF$_3$ | H | 4-[(6-cyanopyridin-3-yl)methoxy]phenyl | |

TABLE 1-continued

Examples of compounds of the formula (I)

| Ex. No. | R¹ | R² | R³ | (structure) | Physical data |
|---|---|---|---|---|---|
| 33 | H | CF$_3$ | H | 4-(6-bromopyridin-3-ylmethoxy)phenyl | |
| 34 | CH$_3$ | CF$_3$ | H | 3-fluoro-4-(6-bromopyridin-3-ylmethoxy)phenyl | |
| 35 | NH$_2$ | CF$_3$ | H | 4-(6-bromopyridin-3-ylmethoxy)phenyl | |
| 36 | H | CF$_3$ | H | 4-(5-cyanopyridin-2-ylmethoxy)phenyl | |
| 37 | CH$_3$ | CF$_3$ | H | 3-fluoro-4-(5-cyanopyridin-2-ylmethoxy)phenyl | |
| 38 | NH$_2$ | CF$_3$ | H | 4-(5-cyanopyridin-2-ylmethoxy)phenyl | |

TABLE 1-continued

Examples of compounds of the formula (I)

| Ex. No. | R¹ | R² | R³ | (structure) | Physical data |
|---|---|---|---|---|---|
| 39 | H | CF$_3$ | H | 4-methylphenyl-O-CH$_2$-(pyridin-2-yl)-5-C(=S)NH$_2$ | |
| 40 | CH$_3$ | CF$_3$ | H | 3-fluoro-4-methylphenyl-O-CH$_2$-(pyridin-2-yl)-5-C(=S)NH$_2$ | |
| 41 | NH$_2$ | CF$_3$ | H | 4-methylphenyl-O-CH$_2$-(pyridin-2-yl)-5-C(=S)NH$_2$ | |
| 42 | H | CF$_3$ | H | 4-methylphenyl-O-CH$_2$-(pyridin-3-yl)-6-C(=S)NH$_2$ | |
| 43 | CH$_3$ | CF$_3$ | H | 4-methylphenyl-O-CH$_2$-(pyridin-3-yl)-6-C(=S)NH$_2$ | |

TABLE 1-continued

Examples of compounds of the formula (I)

| Ex. No. | R¹ | R² | R³ | (structure with (Y)ₙ, Q, Z) | Physical data |
|---|---|---|---|---|---|
| 44 | NH₂ | CF₃ | H | 3-F, 4-methylphenyl–O–CH₂–(pyridin-2-yl with 5-C(=S)NH₂) | |
| 45 | H | CF₃ | H | 3-F, 4-methylphenyl–O–CH₂–(3,5-dimethylisoxazol-4-yl) | m.p.: 205° C. |
| 46 | CH₃ | CF₃ | H | 3-F, 4-methylphenyl–O–CH₂–(3,5-dimethylisoxazol-4-yl) | m.p.: 180° C. |
| 47 | NH₂ | CF₃ | H | 3-F, 4-methylphenyl–O–CH₂–(3,5-dimethylisoxazol-4-yl) | m.p.: 177° C. |
| 48 | H | CF₃ | H | 3-F, 4-methylphenyl–O–CH₂–(tetrahydrofuran-2-yl) | |
| 49 | CH₃ | CF₃ | H | 3-F, 4-methylphenyl–O–CH₂–(tetrahydrofuran-2-yl) | |

TABLE 1-continued
Examples of compounds of the formula (I)
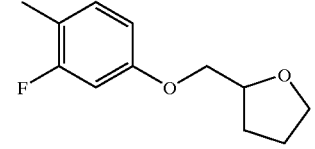
| Ex. No. | R¹ | R² | R³ | 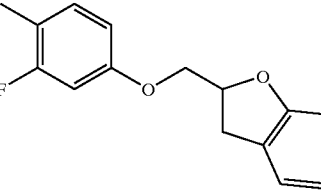 | Physical data |
|---|---|---|---|---|---|
| 50 | NH₂ | CF₃ | H | 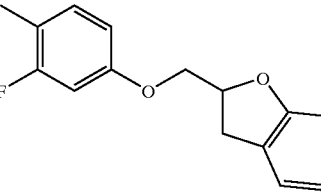 | |
| 51 | H | CF₃ | H | | |
| 52 | CH₃ | CF₃ | H | | |
| 53 | NH₂ | CF₃ | H | | |
| 54 | H | CF₃ | H | 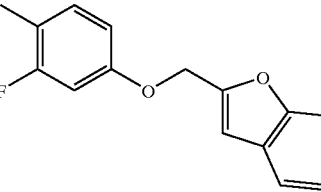 | |
| 55 | CH₃ | CF₃ | H | 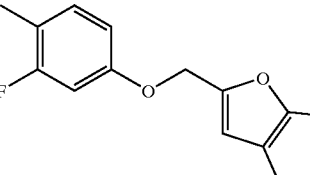 | |

TABLE 1-continued

Examples of compounds of the formula (I)

| Ex. No. | R¹ | R² | R³ | (structure) | Physical data |
|---|---|---|---|---|---|
| 56 | NH$_2$ | CF$_3$ | H | 3-F-4-(benzofuran-2-ylmethoxy)phenyl | |
| 57 | H | CF$_3$ | H | 3-F-4-(furan-2-ylmethoxy)phenyl | |
| 58 | CH$_3$ | CF$_3$ | H | 3-F-4-(furan-2-ylmethoxy)phenyl | |
| 59 | NH$_2$ | CF$_3$ | H | 3-F-4-(furan-2-ylmethoxy)phenyl | |
| 60 | H | CF$_3$ | H | 3-F-4-((1-methylimidazol-2-yl)methoxy)phenyl | |
| 61 | CH$_3$ | CF$_3$ | H | 3-F-4-((1-methylimidazol-2-yl)methoxy)phenyl | |

TABLE 1-continued

Examples of compounds of the formula (I)

| Ex. No. | R¹ | R² | R³ | (structure) | Physical data |
|---|---|---|---|---|---|
| 62 | NH₂ | CF₃ | H | 4-methyl-3-fluoro-phenoxy-CH₂-(1-methylimidazol-2-yl) | |
| 63 | H | CF₃ | H | 4-methyl-3-fluoro-phenoxy-CH₂-(1,3-dioxolan-2-yl) | |
| 64 | CH₃ | CF₃ | H | 4-methyl-3-fluoro-phenoxy-CH₂-(1,3-dioxolan-2-yl) | |
| 65 | NH₂ | CF₃ | H | 4-methyl-3-fluoro-phenoxy-CH₂-(1,3-dioxolan-2-yl) | |
| 66 | H | CF₃ | H | 4-methyl-3-fluoro-phenoxy-CH₂-(2,2-dimethyl-1,3-dioxolan-4-yl) | |
| 67 | CH₃ | CF₃ | H | 4-methyl-3-fluoro-phenoxy-CH₂-(2,2-dimethyl-1,3-dioxolan-4-yl) | |

TABLE 1-continued
Examples of compounds of the formula (I)
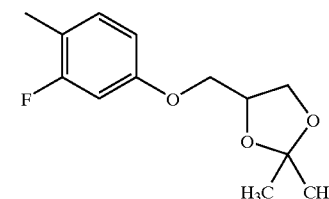
(I)
| Ex. No. | R¹ | R² | R³ | 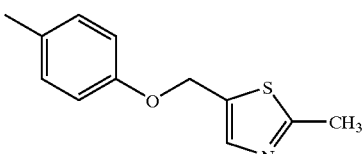 | Physical data |
|---|---|---|---|---|---|
| 68 | NH₂ | CF₃ | H | 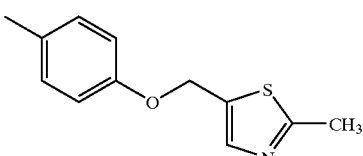 | |
| 69 | H | CF₃ | H | | |
| 70 | CH₃ | CF₃ | H | | |
| 71 | NH₂ | CF₃ | H | 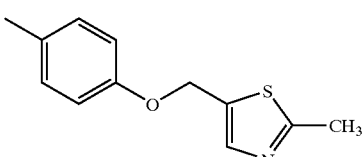 | |
| 72 | H | CF₃ | H | 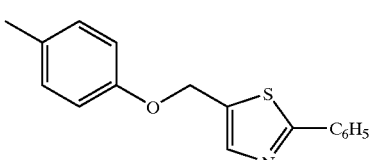 | |
| 73 | CH₃ | CF₃ | H | 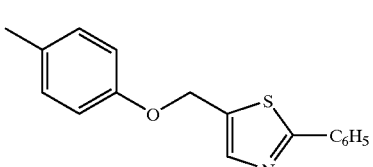 | |

TABLE 1-continued
Examples of compounds of the formula (I)
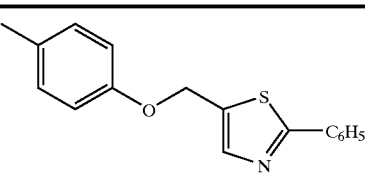
| Ex. No. | R¹ | R² | R³ | | Physical data |
|---|---|---|---|---|---|
| 74 | NH₂ | CF₃ | H | 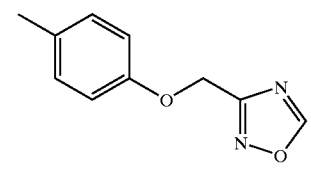 | |
| 75 | H | CF₃ | H | 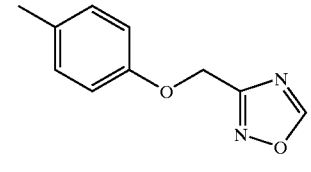 | |
| 76 | CH₃ | CF₃ | H | 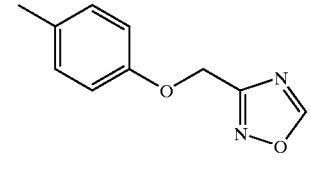 | |
| 77 | NH₂ | CF₃ | H | 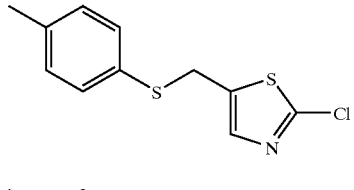 | |
| 78 | H | CF₃ | H | 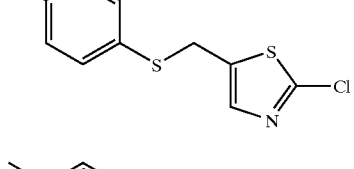 | |
| 79 | CH₃ | CF₃ | H | 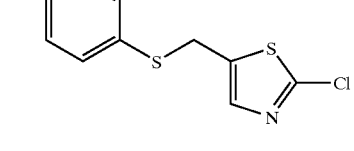 | |
| 80 | NH₂ | CF₃ | H | | |

TABLE 1-continued

Examples of compounds of the formula (I)

| Ex. No. | R¹ | R² | R³ | (substituent structure) | Physical data |
|---------|-----|-----|-----|-------------------------|---------------|
| 81 | H | CF$_3$ | H | 4-[(6-chloropyridin-3-yl)methylthio]phenyl | |
| 82 | CH$_3$ | CF$_3$ | H | 4-[(6-chloropyridin-3-yl)methylthio]phenyl | |
| 83 | NH$_2$ | CF$_3$ | H | 4-[(6-chloropyridin-3-yl)methylthio]phenyl | |
| 84 | H | CF$_3$ | Cl | 4-[(6-chloropyridin-3-yl)methoxy]phenyl | |
| 85 | CH$_3$ | CF$_3$ | CH$_3$ | 4-[(6-chloropyridin-3-yl)methoxy]phenyl | |
| 86 | NH$_2$ | CF$_3$ | CH$_3$ | 4-[(6-chloropyridin-3-yl)methoxy]phenyl | |

TABLE 1-continued
Examples of compounds of the formula (I)
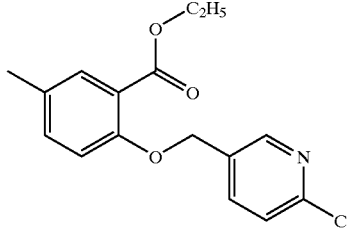
| Ex. No. | R¹ | R² | R³ | | Physical data |
|---|---|---|---|---|---|
| 87 | H | CF$_3$ | H | 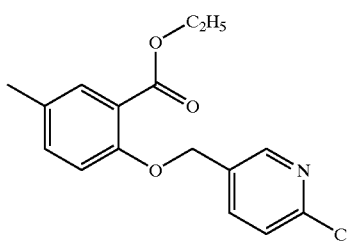 | |
| 88 | CH$_3$ | CF$_3$ | H | 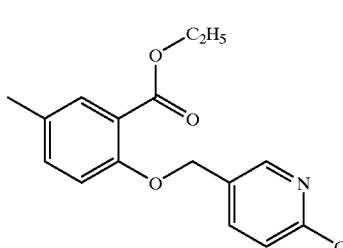 | |
| 89 | NH$_2$ | CF$_3$ | H | 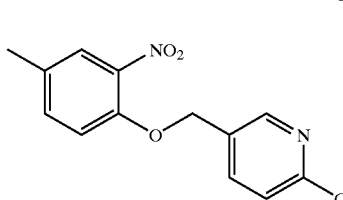 | |
| 90 | H | CF$_3$ | H | 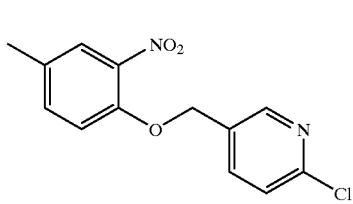 | m.p.: 274° C. |
| 91 | CH$_3$ | CF$_3$ | H | | m.p.: 211° C. |

TABLE 1-continued
Examples of compounds of the formula (I)
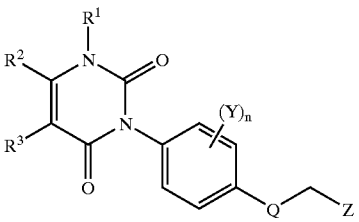
| Ex. No. | R¹ | R² | R³ | 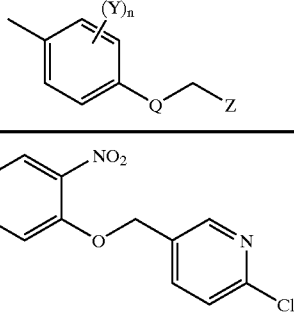 | Physical data |
|---|---|---|---|---|---|
| 92 | NH$_2$ | CF$_3$ | H | 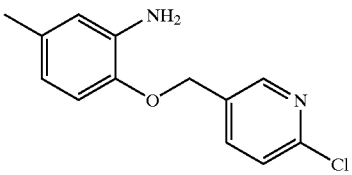 | m.p.: 202° C. |
| 93 | CH$_3$ | CF$_3$ | H | 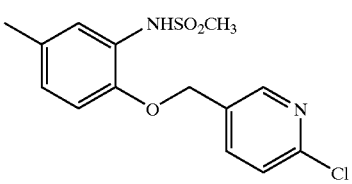 | m.p.: 210° C. |
| 94 | CH$_3$ | CF$_3$ | H | 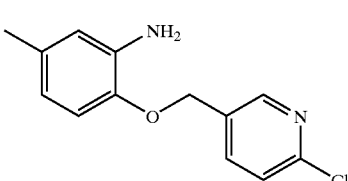 | m.p.: 242° C. |
| 95 | NH$_2$ | CF$_3$ | H | 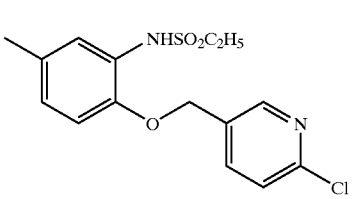 | m.p.: 181° C. |
| 96 | NH$_2$ | CF$_3$ | H | (NHSO$_2$C$_2$H$_5$ substituted phenoxy-methyl-6-chloropyridine) | m.p.: 273° C. |

Starting Materials of the Formula (III)

Example (III-1)

Step 1

A mixture of 8.65 g (55 mmol) of 3-fluoro4-nitro-phenol, 9.72 g (60 mmol) of 2-chloro-5-chloromethyl-pyridine, 8.3 g (60 mmol) of potassium carbonate and 150 ml of butanone is heated at 80° C. for 10 hours and subsequently concentrated under water pump vacuum. The residue is stirred with a solvent mixture comprising aqueous 2N hydrochloric acid, ethyl acetate and diethyl ether, and the resulting crystalline product is isolated by filtration with suction.

This gives 9.8 g (63% of theory) of 2-chloro-5-(3-fluoro-4-nitro-phenoxymethyl)-pyridine of melting point 174° C.

Step 2

9.5 g (33.6 mmol) of 2-chloro-5-(3-fluoro4-nitro-phenoxymethyl)-pyridine are initially charged in a mixture of 150 ml of acetic acid and 10 ml of water and heated to 50° C. 9.5 g of iron (powder) are then added a little at a time, and the reaction mixture is stirred at from 20° C. to 25° C. for approximately 60 minutes and subsequently filtered. The filtrate is concentrated, the residue is shaken with water/ethyl acetate and the organic phase is washed with water, dried with sodium sulphate and filtered. The filtrate is concentrated under water pump vacuum, the residue is digested with petroleum ether and the resulting crystalline product is isolated by filtration with suction.

This gives 7.3 g (86% of theory) of 2-chloro-5-(4-amino-3-fluoro-phenoxymethyl)-pyridine of melting point 101° C.

Step 3

A mixture of 7.0 g (27.7 mmol) of 2-chloro-5-(4-amino-3-fluoro-phenoxymethyl)-pyridine, 3.3 g (27.7 mmol) of ethyl chloroformate, 2.5 g of pyridine and 100 ml of methylene chloride is stirred at 0° C. for 30 minutes and subsequently concentrated under water pump vacuum. The residue is taken up in water, adjusted to pH 2 using 2N hydrochloric acid and stirred with diethyl ether/petroleum ether. The resulting crystalline product is then isolated by filtration with suction.

This gives 8.5 g (99% of theory) of O-ethyl N-[2-fluoro4-(2-chloro-pyridin-5-yl-methoxy)-phenyl]-carbamate of melting point 139° C.

USE EXAMPLES

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way as to apply the particular amounts of active compound desired per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 2 and 3 exhibit, at an application rate of 250 g/ha, strong activity against Alopecurus (95–100%), Setaria (100%), Abutilon (100%), Amaranthus (100%) and Sinapis (100%).

Example B

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction In this test, for example, the compounds of Preparation Examples 2 and 3 exhibit, at an application rate of 250 g/ha, strong activity against Alopecurus (80–90%), Setaria (100%), Abutilon (100%), Amaranthus (100%) and Sinapis (100%).

Example C
Phaedon Larvae Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with mustard beetle larvae (*Phaedon cochleariae*) while the leaves are still moist.

After the desired period of time, the kill in % is determined. 100% means that all beetle larvae have been killed; 0% means that none of the beetle larvae have been killed.

In this test, for example, the compound of preparation example 3 exhibits, at an active compound concentration of 0.1%, a kill of 100% after 7 days.

What is claimed is:

1. A substituted aryluracil of the formula (I)

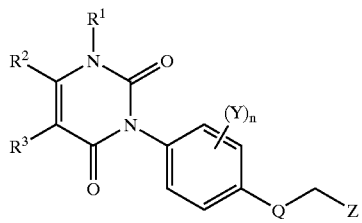

(I)

wherein
n represents the numbers 1, 2 or 3,
Q represents O, S, SO or $SO_2$,
$R^1$ is a moiety selected from the group consisting of hydrogen; amino; unsubstituted alkyl having 1 to 4 carbon atoms; and cyano-, halogen-, or $C_1$–$C_4$-alkoxy-substituted alkyl having 1 to 4 carbon atoms;
$R^2$ is a moiety selected from the group consisting of carboxyl; cyano; carbamoyl; thiocarbamoyl; unsubstituted alkyl having 1 to 4 carbon atoms; unsubstituted alkoxycarbonyl having 1 to 4 carbon atoms; cyano-, halogen- or $C_1$–$C_4$-alkoxy-substituted alkyl having 1 to 4 carbon atoms; and cyano-, halogen- or $C_1$–$C_4$-alkoxy-substituted alkoxycarbonyl having 1 to 4 carbon atoms;
$R^3$ is a moiety selected from the group consisting of hydrogen; halogen; unsubstituted alkyl having 1 to 4 carbon atoms; and halogen-substituted alkyl having 1 to 4 carbon atoms;
Y is halogen, and
Z is a moiety selected from the group consisting of unsubstituted furyl, tetrahydrofuryl, benzofuryl, dihydrobenzofuryl, dioxolanyl, dioxanyl, benzodioxanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, or quinoxalinyl; and substituted furyl, tetrahydrofuryl, benzofuryl, dihydrobenzofuryl, dioxolanyl, dioxanyl, benzodioxanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, thiazolyl, isothiazolyl, benzothiazolyl or benzimidazolyl,
wherein the substituents are selected from the group consisting of nitro; amino; hydroxyl; carboxyl; cyano; carbamoyl; thiocarbamoyl; sulfo; chlorosulfonyl; aminosulfonyl; halogen; $C_1$ to $C_4$ alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino or alkylsulfonylamino; and, cyano-, halogen- or $C_1$–$C_4$-alkoxy-substituted $C_1$–$C_4$ alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino or alkylsulfonylamino; and phenyl.

2. The substituted aryluracil of claim 1, wherein
n represents the numbers 1 or 2,
Q represents O, S, SO or $SO_2$,
$R^1$ is a moiety selected from the group consisting of hydrogen; amino; methyl; ethyl; and cyano-, fluorine-, chlorine-, methoxy-or ethoxy-substituted methyl or ethyl,
$R^2$ is a moiety selected from the group consisting of methyl; ethyl; and fluorine- and/or chlorine-substituted methyl or ethyl,
$R^3$ represents hydrogen, fluorine, chlorine, bromine or methyl,
Y is a moiety selected from the group consisting of fluorine; chlorine; and bromine; and
Z is a moiety selected from the group consisting of furyl; tetrahydrofuryl; benzofuryl; dihydrobenzofuryl; dioxolanyl; pyrrolyl; pyrazolyl; imidazolyl; triazolyl; oxazolyl; isoxazolyl; benzoxazolyl; pyridinyl; quinolinyl; isoquinolinyl; pyrimidinyl; pyrazinyl; pyridazinyl; quinazolinyl; quinoxalinyl; and substituted furyl, tetrahydrofuryl, benzofuryl, dihydrobenzofuryl, dioxolanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, thiazolyl, benzothiazolyl or benzimidazolyl,
wherein the substituents are selected from the group consisting of nitro; amino; hydroxyl; carboxyl; cyano; carbamoyl; thiocarbamoyl; sulfo; chlorosulfonyl; aminosulfonyl; fluorine; chlorine; bromine; methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, methylsulfonyl, ethylsulfonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulfonylamino, ethylsulfonylamino, n- or i-propylsulfonylamino, or n-, i-, s- or t-butylsulfonylamino; cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, methylsulfonyl, ethylsulfonyl, methylamino, ethylamino, n- or i-propylamino, n-, i-, s- or t-butylamino, acetyl, propionyl, n-or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulfonylamino, ethylsulfonylamino, n- or i-propylsulfonylamino, or n-, i-, s- or t-butylsulfonylamino; and phenyl.

3. A substituted aryluracil of the formula (Ia)

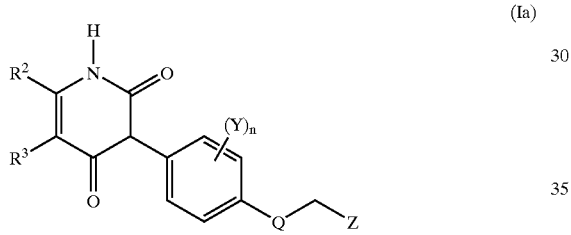

(Ia)

wherein n represents the numbers 1, 2 or 3,

Q represents O, S, SO or $SO_2$, $R^2$ is a moiety selected from the group consisting of carboxyl; cyano; carbamoyl; thiocarbamoyl; unsubstituted alkyl having 1 to 4 carbon atoms; unsubstituted alkoxycarbonyl having 1 to 4 carbon atoms; cyano-, halogen- or $C_1$–$C_4$-alkoxy-substituted alkyl having 1 to 4 carbon atoms; and cyano-, halogen- or $C_1$–$C_4$-alkoxy-substituted alkoxycarbonyl having 1 to 4 carbon atoms;

$R^3$ is a moiety selected from the group consisting of hydrogen; halogen; unsubstituted alkyl having 1 to 4 carbon atoms; and halogen-substituted alkyl having 1 to 4 carbon atoms;

Y is halogen; and

Z is a moiety selected from the group consisting of unsubstituted furyl, tetrahydrofuryl, benzofuryl, dihydrobenzofuryl, dioxolanyl, dioxanyl, benzodioxanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, or quinoxalinyl; and substituted furyl, tetrahydrofuryl, benzofuryl, dihydrobenzofuryl, dioxolanyl, dioxanyl, benzodioxanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, thiazolyl, isothiazolyl, benzothiazolyl or benzimidazolyl, wherein the substituents are selected from the group consisting of nitro; amino; hydroxyl; carboxyl; cyano; carbamoyl; thiocarbamoyl; sulfo; chlorosulfonyl; aminosulfonyl; halogen; $C_1$ to $C_4$ alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino or alkylsulfonylamino; and, cyano-, halogen- or $C_1$–$C_4$-alkoxy-substituted $C_1$–$C_4$ alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino or alkylsulfonylamino; and phenyl.

4. The compound of claim 2, wherein n represents the numbers 1 or 2,

Q represents O, S, SO or $SO_2$, $R^2$ is a moiety selected from the group consisting of methyl; ethyl: and fluorine- and/or chlorine-substituted methyl or ethyl, $R^3$ represents hydrogen, fluorine, chlorine, bromine or methyl, Y is a moiety selected from the group consisting of fluorine; chlorine; and bromine; and Z is a moiety selected from the group consisting of furyl; tetrahydrofuryl; benzofuryl; dihydrobenzofuryl; dioxolanyl; pyrrolyl; pyrazolyl; imidazolyl; triazolyl; oxazolyl; isoxazolyl; benzoxazolyl; pyridinyl; quinolinyl; isoquinolinyl; pyrimidinyl; pyrazinyl; pyridazinyl; quinazolinyl; quinoxalinyl; and substituted furyl, tetrahydrofuryl, benzofuryl, dihydrobenzofuryl, dioxolanyl, pyrrolyl, pyrazolyl, imidazolyl, triazolyl, oxazolyl, isoxazolyl, benzoxazolyl, pyridinyl, quinolinyl, isoquinolinyl, pyrimidinyl, pyrazinyl, pyridazinyl, quinazolinyl, quinoxalinyl, thiazolyl, benzothiazolyl or benzimidazolyl, wherein the substituents are selected from the group consisting of nitro; amino; hydroxyl; carboxyl; cyano; carbamoyl; thiocarbamoyl; sulfo; chlorosulfonyl; aminosulfonyl; fluorine; chlorine; bromine; methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, methylsulfonyl, ethylsulfonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulfonylamino, ethylsulfonylamino, n- or i-propylsulfonylamino, or n-, i-, s- or t-butylsulfonylamino; cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, methylsulfonyl, ethylsulfonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulfonylamino, ethylsulfonylamino, n- or i-propylsulfonylamino, or n-, i-, s- or t-butylsulfonylamino; and phenyl.

5. A herbicidal composition, comprising one or more substituted aryluracils of Formula I of claim 1 and a member selected from the group consisting of extenders, surfactants and mixtures thereof.

* * * * *